United States Patent [19]

Jiles

[11] Patent Number: 5,394,083

[45] Date of Patent: Feb. 28, 1995

[54] MAGNETIC IMAGING SYSTEM FOR DISPLAY OF LOCAL VARIATIONS OF MAGNETIC PROPERTIES IN MAGNETIC MATERIAL

[75] Inventor: David C. Jiles, Ames, Iowa

[73] Assignee: Iowa State University Research Foundation, Inc., Ames, Iowa

[21] Appl. No.: 932,896

[22] Filed: Aug. 20, 1992

[51] Int. Cl.$^6$ .................... G01R 33/12; G01R 33/14; G01N 27/72

[52] U.S. Cl. .................... 324/223; 324/226; 324/227; 324/240; 364/481

[58] Field of Search .................... 324/209, 214–216, 324/222, 223, 226, 227, 232, 233–243; 358/82, 107; 364/413.13, 413.22, 413.25, 481, 550, 556; 348/32–34, 162

[56] References Cited

U.S. PATENT DOCUMENTS

| | | | |
|---|---|---|---|
| 2,617,854 | 11/1952 | Van Valkenburg | 175/183 |
| 3,109,139 | 10/1963 | Branker | 324/34 |
| 3,311,818 | 3/1967 | Quittner | 324/34 |
| 3,427,872 | 2/1969 | Leep et al. | 73/88.5 |
| 3,612,986 | 10/1971 | Rollwitz | 324/34 |
| 3,742,357 | 6/1973 | Kubo et al. | 324/34 |
| 3,826,132 | 7/1974 | Fetner et al. | 73/143 |
| 3,861,206 | 1/1975 | Kawafune et al. | 73/141 |
| 3,925,724 | 12/1975 | Steingroever | 324/34 |
| 3,976,935 | 8/1976 | Steingroever | 324/34 |
| 4,095,181 | 6/1978 | Harris et al. | 324/238 |
| 4,316,146 | 2/1982 | Jilken | 324/209 |
| 4,379,261 | 4/1983 | Lakin | 324/240 |
| 4,463,313 | 7/1984 | Steingroever et al. | 324/243 |
| 4,493,039 | 1/1985 | Gregory | 364/414 |
| 4,495,466 | 1/1985 | Lakin | 324/242 |
| 4,528,856 | 7/1985 | Junker et al. | 73/779 |
| 4,534,405 | 8/1985 | Hulek et al. | 324/203 |
| 4,631,533 | 12/1986 | Mark, Jr. | 324/233 X |
| 4,634,976 | 1/1987 | Tiitto | 324/240 |
| 4,648,041 | 3/1987 | Tarr | 364/481 |
| 4,855,677 | 8/1989 | Clark, Jr. et al. | 324/238 |
| 4,881,030 | 11/1989 | Stuecker et al. | 324/209 |
| 4,931,730 | 6/1990 | Olsen et al. | 324/209 |
| 4,987,367 | 1/1991 | Ishikawa et al. | 324/223 X |
| 4,990,851 | 2/1991 | Spies | 324/242 X |
| 5,008,621 | 4/1991 | Jiles | 324/227 |
| 5,010,299 | 4/1991 | Nishizawa et al. | 324/209 |
| 5,028,100 | 7/1991 | Valleau et al. | 324/232 |
| 5,059,903 | 10/1991 | Otaka et al. | 324/223 |

FOREIGN PATENT DOCUMENTS 685727 5/1964 Canada .................... 324/373

*Primary Examiner*—Gerard R. Strecker
*Attorney, Agent, or Firm*—Leydig, Voit & Mayer, Ltd.

[57] ABSTRACT

A multiparameter magnetic imaging system and method to be used in the localized measurement of the magnetic properties of a material and the display of those properties in the form of a false color image indicating the occurrence of those properties across the surface of a sample specimen. The system includes an inspection probe to measure certain magnetic parameters across the surface of the specimen and means to determine a multiplicity of magnetic property values based on the measured data. The system also includes a visual display system which selectively displays the data relating to the determined magnetic properties in the form of a false color image indicating the presence and variation of these magnetic properties across the specimen surface.

19 Claims, 3 Drawing Sheets

MAGNETIC IMAGING SYSTEM FOR DISPLAY OF LOCAL VARIATIONS OF MAGNETIC PROPERTIES IN MAGNETIC MATERIAL

GRANT REFERENCE

This invention was made with Government support under Contract No. ITA 87-02 awarded by U.S. Department of Commerce. The Government has certain rights in the invention.

FIELD OF THE INVENTION

The present invention relates generally to systems for the localized evaluation of the magnetic properties of a material and more particularly to a system and method for deriving and displaying a multidimensional color representation of the magnetic properties occurring across the surface of a material specimen.

BACKGROUND OF THE INVENTION

It is often desirable to evaluate the properties of a material without damaging the specimen being tested. Several known techniques make use of magnetism to evaluate specific properties in a specimen sample. Such evaluation techniques include eddy-current testing, magnetic particle inspection and flux leakage inspection. Such techniques, however, provide only limited information regarding the properties of the material under evaluation.

Magnetic particle inspection and flux leakage inspection represent well known magnetic evaluation techniques. These techniques permit detection of cracks and pitting due to the perturbance of magnetic flux caused by such inhomogeneities. These techniques, however, are unsuitable for the identification and measurement of discontinuities in material properties such as stress or fatigue which produce subtle changes in the characteristics of a material.

The ability to obtain more meaningful information regarding a material's less pronounced intrinsic properties through measurement of magnetic properties has been recently recognized by those skilled in the art. For example, it is known that coercivity can be used to detect plastic deformation and hardness, that maximum differential permeability can be used to measure stress, that remanence can be used to detect creep damage, that a combination of remanence and coercivity can be used to detect impending fatigue failure and that hysteresis loss can be used to detect changes in grain boundary segregation arising from temper embrittlement.

This ability to correlate the magnetic characteristics of a material to its less pronounced intrinsic physical properties is disclosed in U.S. Pat. Nos. 5,008,621 and 5,012,189 both of which issued to the present inventor.

As recognized in the art and taught by both the '621 patent and the '189 patent, bulk magnetic properties such as coercivity, remanence, hysteresis loss, initial permeability, maximum differential permeability and anhysteretic permeability may be derived from magnetic hysteresis curves. As is well known, the magnetic hysteresis curve is a plot of flux density B in a material versus a varying applied magnetic field intensity H. Both the '621 patent and the '189 patent further teach that information regarding the physical properties of a sample specimen may be obtained from the evaluation of the magnetic properties occurring therein.

The '189 patent entitled "Method for Deriving Information Regarding Stress from a Stressed Ferromagnetic Material" is illustrative of one type of physical data which can be derived from magnetic measurements. Specifically, the '189 patent discloses the ability to derive a meaningful estimate of the actual and residual stress in a material based on the hysteresis and anhysteretic magnetization curves at the origin as compared to such curves in an unstressed sample.

The system and method disclosed in U.S. Pat. No. 5,059,903 to Otaka et al. illustrates another type of physical data which may be derived from magnetic measurements. As disclosed in the Otaka patent, the embrittlement of a material can be evaluated through comparison of the magnitude of magnetization characteristics measured in a sample specimen to the magnetic characteristics of a virgin specimen. By making these comparative analyses on a periodic basis, it is possible to determine degradation rates as well as to identify areas in which degradation is most severe.

While useful in evaluating a specific property of the specimen, namely embrittlement, it will be appreciated that the Otaka patent does not provide for the evaluation of a broad scope of material properties such as hardness, internal stress or grain boundary segregation which may be of interest.

The system and method disclosed in the '621 patent to the present inventor provides a useful means to evaluate the bulk magnetic properties occurring in a sample as a whole without the need to make a comparison to virgin material as is required by the Otaka patent. As disclosed in the '621 patent, this bulk analysis is effected by subjecting an entire sample to a variable magnetic field and taking multiple measurements of the magnetic field and the magnetic flux of the specimen as the magnetic field is cycled in a controlled manner. As will be recognized, such a controlled cycling permits the collection of data sufficient to generate a hysteresis curve.

The system and method of the '621 patent are useful in generating information relative to the sample as a whole. However, due to the need to surround the sample with a magnetic field, no information is obtained regarding differences in a material's magnetic properties, and hence physical characteristics, occurring across the specimen surface. Further, the '621 patent incorporates no means to display data relating to the magnetic properties occurring across an area of the sample specimen.

SUMMARY OF THE INVENTION

In view of the foregoing, it is a general object of the present invention to provide a system and method to produce a false color image of a sample specimen displaying the magnetic properties present across the surface of a sample specimen.

In that respect, it is an object of the present invention to provide a system and method which allows the scanning determination of multiple magnetic properties across the surface of the specimen sample.

It is a further object of the present invention to provide a system and method which permits the magnetic properties measured across the surface to be related to positions on the specimen surface.

It is yet a further object of the present invention to provide a system and method which permits the display of selected magnetic properties or combinations of properties present across the surface of the specimen sample in the form of a false color image indicating the magnitude of the magnetic property or combination and a positional relation to the surface of the specimen.

Accordingly, it is a feature of the present invention to provide a system and method for scanning measurement of multiple magnetic properties across the surface of a sample specimen.

It is an additional feature of the present invention that the position of the probe during scanning measurement is identified.

It is a further feature of the present invention that the position of the probe during scanning measurement is correlated to the magnetic properties measured during the scan.

It is yet another feature of the present invention that a false color image is displayed illustrating the magnitude and variation of magnetic properties across the surface of the sample specimen.

It is yet a further feature of the present invention that multiple images illustrating multiple magnetic properties may be displayed.

In accordance with one aspect of the present invention, a multiparameter magnetic imaging system for deriving and displaying a multidimensional color representation of the magnetic properties of a material is provided. The multiparameter imaging system comprises a magnetic inspection probe making multiple scanning measurements of magnetic data at a plurality of locations across a specimen surface, means for correlating magnetic data to locations on the specimen surface, means for deriving magnetic properties of the specimen and means for displaying a false color image illustrating the presence and variation of magnetic properties across the specimen surface.

In another aspect of the present invention, a method for carrying out the magnetic evaluation of a material is provided. The method comprises the steps of measuring magnetic parameters of a material at locations across the surface of a material specimen, determining the magnetic properties of the material across the surface of the specimen and displaying a false color image of the specimen surface illustrating the presence and variation of magnetic properties.

In a related aspect of the present invention, a method for carrying out the magnetic evaluation of a material is provided wherein multiple images are displayed of the specimen surface illustrating multiple magnetic properties.

While the invention will be described and disclosed in connection with certain preferred embodiments and procedures, it is not intended to limit the invention to those specific embodiments. Rather it is intended to cover all such alternative embodiments and modifications as fall within the spirit and scope of the invention as defined by the appended claims.

DETAILED DESCRIPTION OF THE PREFERRED EMBODIMENT

Figure 1:
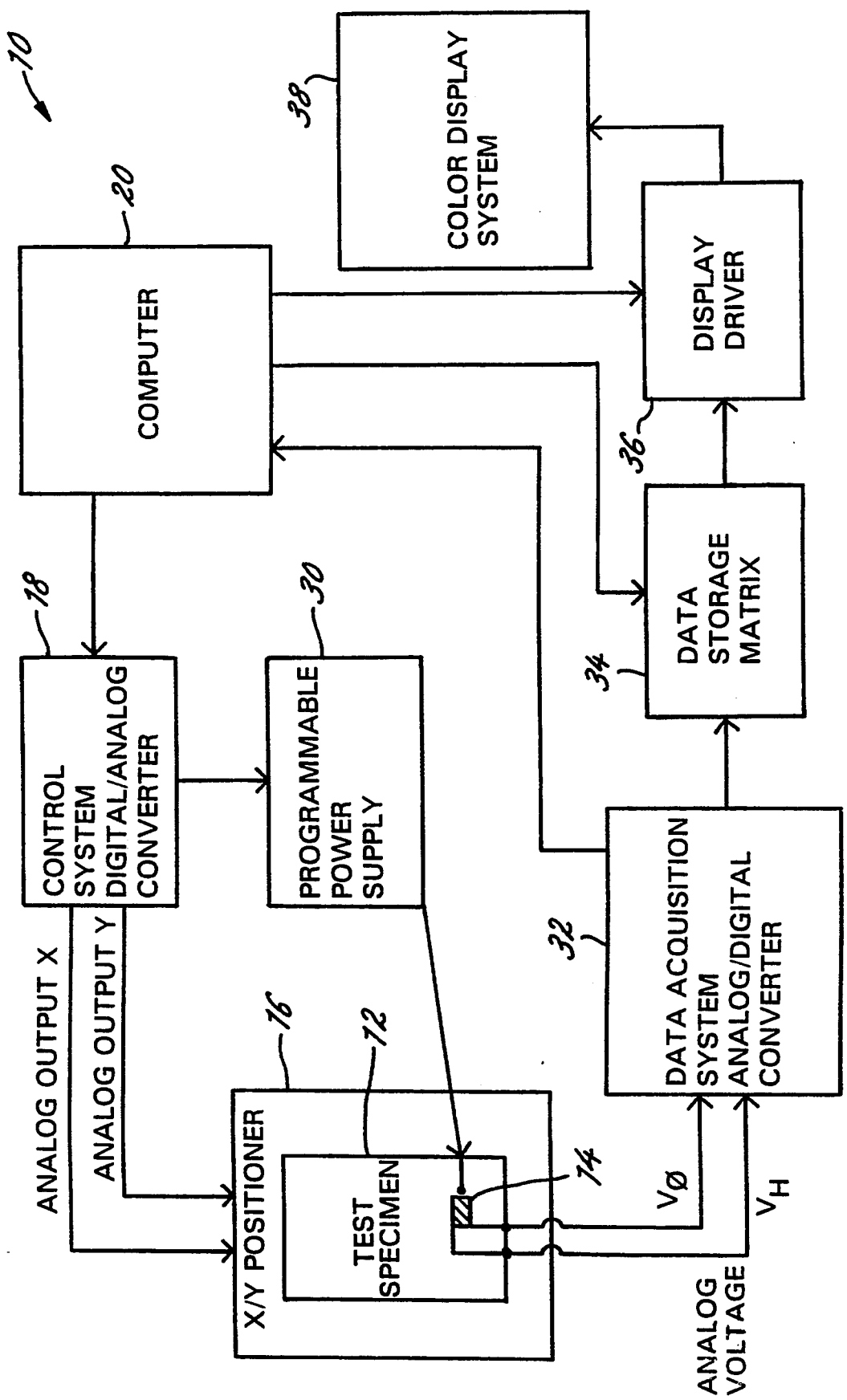
FIG. 1 is a block diagram of a preferred embodiment of the present invention.

Turning now to the drawings, a preferred embodiment of the magnetic imaging system of the invention is shown in FIG. 1 and generally designated by reference numeral 10. As shown, a test specimen 12 may be scanned by means of a moveable magnetic probe 14.

As will be appreciated, this scanning operation may be effected in numerous ways. For example, the probe 14 may be moved across the surface of the specimen by manual means, by application of an analog voltage signal to a potentiometer based positioning arrangement or moved in a controlled manner by an attached stepper motor which moves the probe 14 in a known manner. In fact, any probe positioning means may be incorporated for use in the present invention so long as an indication of probe position during measurement is provided. For example, if the probe 14 is moved manually across the surface of the specimen 12, or by a motor without a closed loop feedback control, a positioning encoder coupled to the probe can produce signals of probe position during measurement. This information is entered into a computer 20 for correlation to the multiple magnetic properties measured across the surface of the specimen 12 as described more fully below.

Figure 2A:
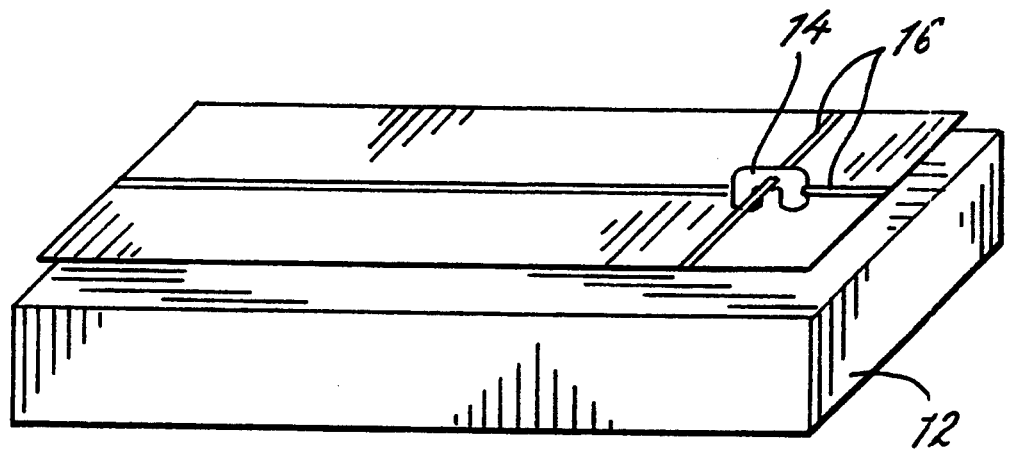
FIG. 2A is a perspective view of the positional scanner and magnetic inspection probe of the present invention scanning a sample specimen.
Figure 2B:
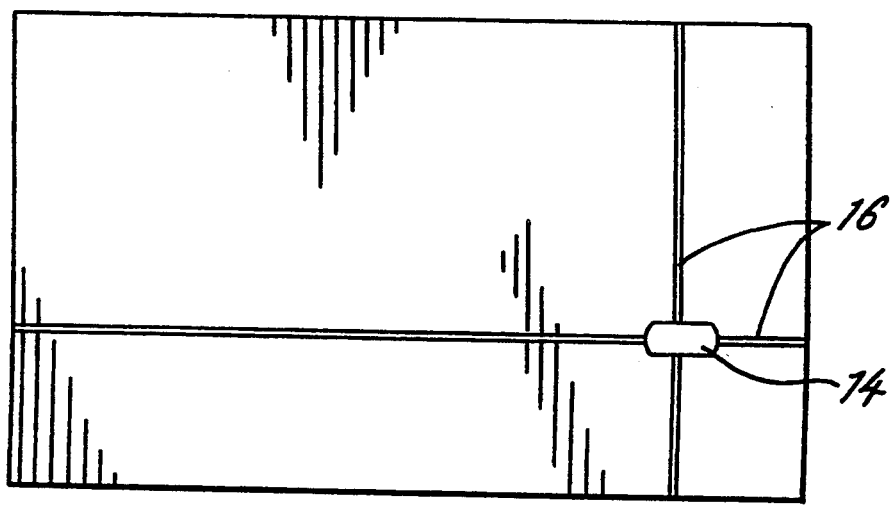
FIG. 2B is a top view of the positional scanner and magnetic inspection probe of FIG. 2A.

While any positioning means which permits the location of the probe to be identified during measurement is within the scope of the present invention, in the preferred embodiment the inspection probe 14 will be scanned across the surface of the specimen 12 by means of an X/Y positioner 16 controlled by means of analog voltage signals. A preferred embodiment of the X/Y positioner 16 is illustrated in FIGS. 2A–B. It will be noted that while reference is made to the X/Y positioner 16, movement of the probe 14 is not limited to a rectilinear coordinate designation system. Rather, any appropriate coordinate system may be utilized.

As illustrated, the X/Y positioner 16 is preferably controlled by analog outputs generated by a control system 18. The control system 18, in turn, is driven by a digital signal generated by a computer processor 20 which is programmed in a known manner to cause the X/Y positioner 16 to move the magnetic inspection probe 14 across the sample.

In the preferred embodiment, the magnetic inspection probe 14 is capable of generating highly resolved data. That is, as discussed below, the inspection probe 14 is capable of limiting the measurement of magnetic parameters to within a relatively small surface area. Preferably, this resolution of measurement will be on the order of approximately 1 millimeter square. Thus, in the preferred embodiment, the positioning means utilized will be able to position the probe with at least the same level of precision as the probe resolution.

Figure 3A:
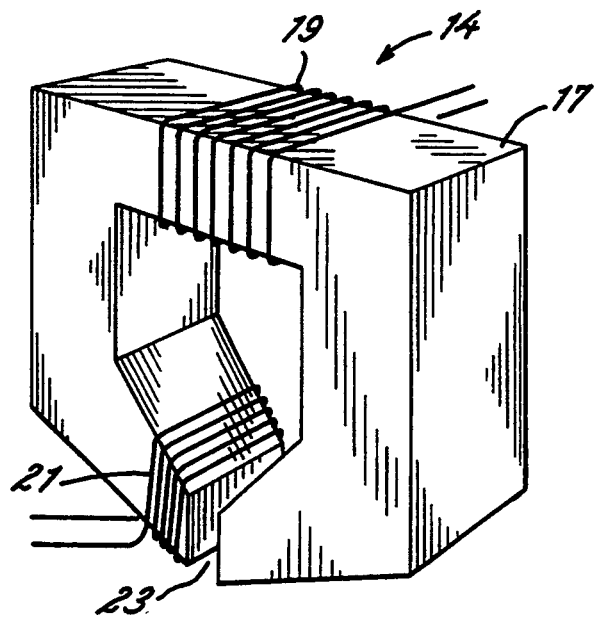
FIG. 3A is a perspective view of a typical narrow aperture magnetic inspection head for use in the present invention.
Figure 3B:
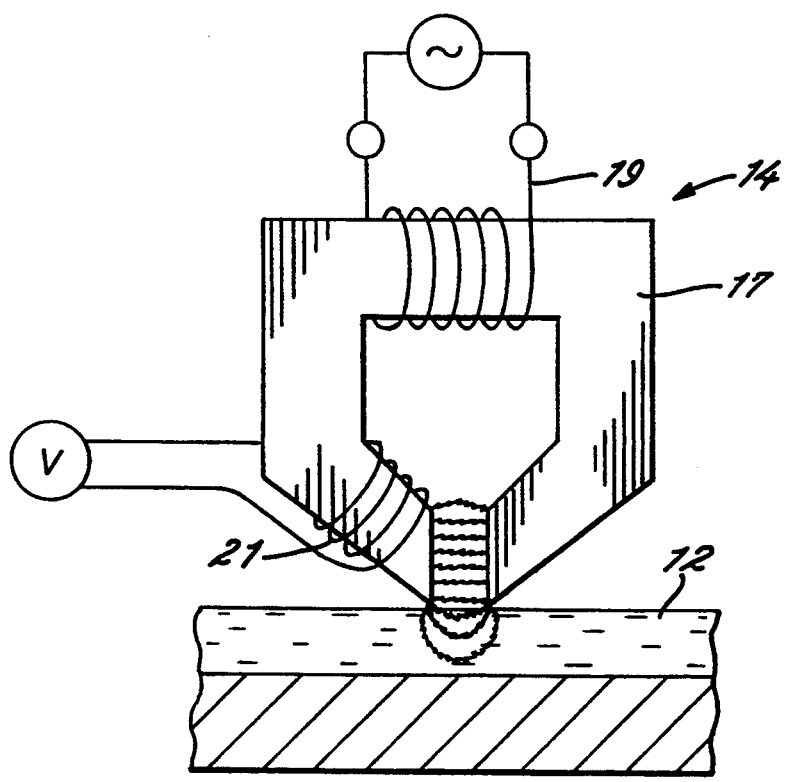
FIG. 3B is a side view of the narrow aperture inspection probe of FIG. 3A illustrating the lines of magnetism in a sample specimen.

In order to generate the highly resolved data which is desirable in the present invention, a narrow aperture unidirectional magnetic probe is generally utilized. One potential embodiment of such a probe is illustrated in FIGS. 3A–B. The technology for such high resolution probes is known in the art, although prior to the present invention the use of such technology has not been extended to the comprehensive evaluation of the magnetic properties present across a specimen surface.

In the preferred embodiment, inspection probe 14 is capable of generating a controllably varying magnetic field while at the same time taking multiple measurements of field strength and magnetic flux in the specimen. Accordingly, the high resolution magnetic probe 14 utilized in the preferred embodiment includes a field generating power coil, means for detecting field strength and means for measuring magnetic flux in the specimen. The field detection means may consist of the field generating coil if the coil is controlled in a known manner by means such as a programmable power supply as described more fully below. Alternatively, a separate detection device such as a Hall probe or superconducting quantum interference device (SQUID) may be used if appropriate. In the preferred embodiment, magnetic flux will be measured by means of a tape recorder read/write head as known in the art and illustrated in FIGS. 3A-3B. Alternative flux measurement means capable of measuring magnetic flux in the specimen with sufficient precision may also be employed.

One embodiment of an inspection probe for use in the system and method of the present invention is illustrated in FIGS. 3A-B. As illustrated, the inspection probe typically includes a body portion 17, a power coil 19, and a flux detection coil 21. As illustrated, the body portion 17 preferably has a narrow aperture 23 disposed therein. As will be appreciated, this narrow aperture gap permits the collection of highly resolved specimen flux data by the flux detection coil 21. In the embodiment illustrated, the power coil 19 is used to control and monitor the magnetic field. As previously indicated, however, inspection probe 14 may also incorporate other means, such as a Hall probe (not shown) to provide an independent measure of field intensity.

As most clearly indicated through reference to FIG. 3B, the narrow aperture probe 14 is preferably passed very close to the surface of the specimen 12 during measurement. This permits the magnetic field to be applied to the specimen in a precise manner thereby permitting high resolution readings across the narrow aperture gap 23.

In order to determine the values for multiple magnetic properties across the surface of the specimen, the magnetic field generated by the field coil of the probe 14 is preferably cycled through a range of values sufficient to generate a full hysteresis loop for the material under evaluation. Thus, at each instance of probe measurement, a plurality of data points representing the field intensity H and the flux density B is collected.

In order to cycle the magnetic field through the desired range of values, a programmable power supply 30 is preferably utilized. In the preferred embodiment, the programmable power supply 30 is controlled by means of control system 18, which in turn is controlled by a digital output from computer 20 based on commands which may be preprogrammed. Measurements of field intensity and flux density are conveyed to a data acquisition system 32 as analog voltage signals, $V_H$ and $V_\phi$ respectively. As discussed previously, field intensity H may be determined either by means of the known controlled relation between the power supply 30 and the field generating power coil 19 or by separate means such as a Hall probe.

Importantly, numerous voltage signals will be generated at each point of probe measurement as the field intensity is cycled over a range of values by means of the programmable power supply 30. By collecting data over a full cycle of field intensity values, it is possible to generate data sufficient to construct a full hysteresis loop. This data may thereafter be utilized to determine the values for multiple magnetic properties at any location across the surface of the specimen since such properties are defined by the hysteresis loop in a well known manner.

The voltage signals generated by the magnetic probe 14 are preferably transmitted to a data acquisition system 32 which collects the data and converts the analog voltage signals to digital form suitable for storage and computer processing. Data acquisition systems which are well known in the art may be utilized. One such acquisition system which may be utilized is the Labmaster system which is distributed by Tecmar Incorporated of Solon, Ohio. This system utilizes a ±10 Volt output with a 0.005 Volt resolution and a 12 bit A/D converter.

The digital signals generated by the data acquisition system 32 are transmitted to the computer 20 for processing. If the magnetic probe 14 is positioned by means other than program commands generated by the computer 20, the data acquisition means may also be used to collect positional data from these positioning means for eventual transmission to the computer.

Once the digital signals representing field intensity and flux density have been transmitted from the data acquisition system 32 to the computer 20, these measurements are combined and correlated according to well known relationships to derive values for a number of magnetic properties. As indicated previously, these magnetic properties can all be determined from the data relating to field intensity and flux density and include coercivity, remanence, hysteresis loss, initial permeability, maximum differential permeability and differential permeability at remanence. Accordingly, the computer 20 may be preprogrammed to carry out the calculations necessary to derive each of the desired magnetic parameters occurring at any position across the specimen surface.

For example, permeability $\mu = B/H$, differential permeability $\mu' = dB/dH$. Coercivity $H_c$ and remanence $B_r$ are calculated by analyzing the hysteresis loop data close to B=0 and H=0 respectively.

The value of the hysteresis loss ($W_H$) is calculated by integration around the hysteresis loop. Initial and anhysteretic permeabilities $\mu'_{in}$ and $\mu'_{an}$ are obtained using linear least-squares analysis of data at the origin H=0, B=0. Maximum differential permeability $\mu'_{max}$ is calculated from the slope of the hysteresis loop at $H_c$, B=0.

As previously indicated, in the preferred embodiment of the invention the computer 20 controls the position of the magnetic inspection probe 14 during the scanning measurements of magnetic properties. Accordingly, the position of the probe 14 relative to the surface of the specimen is known at any point and it is therefore possible to correlate the magnetic properties of the specimen determined by the above relationships to locations across the specimen surface. Alternatively, if the computer 20 is not used to control the position of the magnetic probe 14, data relating to the position of the probe may be obtained by other means. For example, as indicated above, the probe positional data may be entered into the computer manually or may be passed as a voltage signal through data acquisition system 32.

In an important aspect of the present invention, the computer 20 is preferably used to develop a multidimensional matrix indexing magnetic properties to locations across the surface of the specimen. Hence for any location on the specimen surface, multiple magnetic properties may be known. This data may be stored on storage means 34 such as a hard disk or other suitable means as are well known in the art and later retrieved for evaluation at any desired time.

It should be noted that the correlation between magnetic properties and surface location is extremely flexible. Thus, while the magnetic properties may be indexed directly to the position where such properties were measured, such a direct one-to-one correspondence is not absolutely necessary. In fact, any useful correlation between magnetic properties and surface location may be utilized and is considered to be within the scope of the invention.

In another important aspect of the present invention, the data calculated with respect to the various magnetic material properties can be displayed by means of a color monitor as a "false color image" illustrating multiple magnetic properties or combinations of properties as they occur across the surface of the sample specimen. The term "false color image" is used to describe an image of the sample surface illustrating the magnetic properties which are present across that surface by means of color and shading. The image is described as being "false" due to the fact that the actual physical appearance of the specimen is not illustrated. Rather, what is seen in the image as color are the magnetic characteristics of the sample as they occur across any defined surface of the sample specimen.

In the preferred operation of this display feature, the positional and magnetic data which has been correlated by the computer 20 is retrieved from storage means 34 and converted to a digitized color code by means of a display driver 36. The digitized code data may thereafter be transmitted to a color display system 38 for illustration of the magnetic property values occurring across the specimen surface. This illustration is performed by drawing the color coded data in pixels on the display at X/Y screen positions illustrating the relation of the magnetic properties to positions on the specimen surface.

In the preferred embodiment, the display driver 36 will be controlled by the computer 20 or other suitable control means which in turn are controlled by the operator through commands to retrieve and display meaningful selected data.

Importantly, once the data relating to scanning position and magnetic properties has been collected and correlated, it is possible to display an image illustrating the occurrence and variation of any magnetic property over any defined surface area. For example, an image could be displayed illustrating a magnetic property or combination of properties of interest across the entire specimen surface so as to provide a broad overview of the variation in these properties within the specimen. Likewise, any property of interest could be displayed across a small area so as to clearly identify the exact location of any discontinuities in the sample specimen. Thus, multiple images can be displayed illustrating multiple parameters of interest.

In accordance with the above description, it is seen that the present invention provides a system and method for use in the localized measurement of the magnetic properties of a material. This invention is particularly useful in the evaluation of ferromagnetic materials. More specifically, a system and method are provided for deriving and displaying a color representation of the magnetic properties across the surface of a sample specimen.

I claim as my invention:

1. A multiparameter magnetic imaging system for deriving and displaying a multidimensional color representation of intrinsic magnetic properties of a material derived from a plurality of hysteresis measurements, the system comprising in combination:
   means including an inspection probe for subjecting localized areas of a specimen of the material to a magnetic field and measuring the localized response of the specimen,
   control means associated with the inspection probe for controllably varying the strength of the magnetic field to produce and store localized hysteresis measurements;
   means for scanning said probe over the surface of the specimen for taking a sequence of localized hysteresis measurements at each of a plurality of locations across the specimen surface;
   means for correlating said localized hysteresis measurements to the locations on said specimen surface at which the measurements were taken;
   means for deriving values for at least one intrinsic magnetic property for the respective locations of the specimen from said localized hysteresis measurements; and
   means for displaying a false color image of the surface of the specimen in which the color displayed for the surface at each respective location is related to the value of the derived intrinsic magnetic property at the respective locations, to produce a color map of the specimen surface displaying the variation of the derived intrinsic magnetic property across said specimen surface.

2. The system of claim 1 wherein:
   the means for deriving derives values for a plurality of intrinsic magnetic properties for each respective location from said localized hysteresis measurements; and
   the means for displaying assigns respective colors to the respective derived intrinsic magnetic properties to cause the false color image to distinguish therebetween.

3. The system of claim 1, wherein said control means for controlling the magnetic field comprises a programmable power supply.

4. The system of claim 1, further comprising data acquisition means for collecting and storing the localized hysteresis measurements collected by said inspection probe.

5. The system of claim 1, wherein said means for correlating the localized hysteresis measurements to locations across said specimen surface comprise a computer.

6. The system of claim 1, further comprising data storage means for storing magnetic and positional data.

7. The system of claim 1, wherein said magnetic property displayed on said false color image is selected from the group which includes coercivity, remanence, hysteresis loss, initial permeability, maximum differential permeability and differential permeability at remanence.

8. The system of claim 1, further comprising positioning means for positioning the probe across said specimen surface.

9. A multiparameter magnetic imaging system for deriving and displaying a multi-dimensional color representation of intrinsic magnetic properties occurring across the surface of a specimen derived from a plurality of hysteresis measurements, the system comprising in combination:

an inspection probe for generating and measuring a magnetic field and measuring magnetic flux in localized areas of the specimen;

a control system for controlling the power supplied to said inspection probe at a plurality of levels to generate a controllably variable magnetic field;

acquisition means for collecting the magnetic field and flux data measured by said inspection probe to produce localized hysteresis measurements;

means for scanning the inspection probe across the surface of the specimen to cause the acquisition means to collect the localized hysteresis measurements for a plurality of locations across the surface as the inspection probe is scanned over said surface;

means for deriving values for at least one intrinsic magnetic properties for the respective locations of the specimen from the localized hysteresis measurements;

means for correlating the derived intrinsic magnetic property values of the specimen to the locations across the specimen surface at which the hysteresis measurements were made;

means for storing data representative of said derived intrinsic property values in indexed relation to said locations across the specimen surface; and means for displaying a false color image of the specimen surface in which the color displayed for the surface at the respective locations is related to the values of the derived intrinsic magnetic property.

10. The system of claim 9, wherein said magnetic property displayed on said false color image is selected from a group which includes coercivity, remanence, hysteresis loss, initial permeability, maximum differential permeability and differential permeability at remanence.

11. The system of claim 9, further comprising scanning means to scan said inspection probe across said specimen surface.

12. The system of claim 9 in which:
the means deriving derives a plurality of intrinsic magnetic properties for the respective locations of the specimen from the hysteresis measurements; and
the means for displaying produces false color images for the respective derived intrinsic magnetic properties which distinguish between the derived intrinsic magnetic properties.

13. A method for carrying out the localized measurement of intrinsic magnetic properties of a material derived from a plurality of hysteresis measurements, comprising the steps of:
scanning over a surface of a specimen of the material and taking localized hysteresis measurements of the specimen at a plurality of locations across the surface of the specimen;
determining from the hysteresis measurements at the respective locations values for at least one intrinsic magnetic property of the specimen across the surface thereof;
correlating the determined intrinsic magnetic property to the locations at which the hysteresis measurements were taken; and
displaying a false color image of the surface of the specimen in which the color displayed for the surface at the respective locations is related to the value of the intrinsic magnetic property at the respective locations, to produce a color map of the specimen surface displaying the variation of the determined intrinsic magnetic property.

14. The method of claim 13, wherein the hysteresis measurements across the surface of the specimen are measurements of field strength and magnetic flux in the specimen.

15. The method of claim 14, wherein the determined magnetic property is selected from a group which includes coercivity, remanence, hysteresis loss, initial permeability, maximum differential permeability and differential permeability at remanence.

16. The method of claim 13 wherein:
the determining step determines a plurality of intrinsic magnetic properties across the surface of the specimen from the hysteresis measurements; and
the displaying step assigns different colors to the false color image of the specimen for the respective determined intrinsic magnetic properties to distinguish therebetween.

17. A method for carrying out the localized measurement of intrinsic magnetic properties of a material derived from a plurality of hysteresis measurements, comprising the steps of:
(a) scanning the surface of a specimen of the material by:
(i) applying a magnetic field to a plurality of locations across the surface of the specimen;
(ii) identifying coordinates of each said location of the field application;
(iii) measuring the magnetic flux in the material in response to the application of the magnetic field at each said location; and
(iv) controllably varying the magnetic field at each said location to produce localized hysteresis measurements at said location;
(b) determining localized values for the at least one intrinsic magnetic property of the material at each said location from the magnetic flux and magnetic field hysteresis measurements raked across the specimen surface at said locations;
(c) indexing the determined intrinsic magnetic property to the coordinates of the locations on the specimen surface at which the measurements were taken; and
(d) displaying a false color image of the specimen surface in which the color displayed for the surface at the respective locations is related to the values of the intrinsic magnetic property at the respective locations, to produce a color map of the specimen surface displaying the variation of the determined intrinsic magnetic property across the surface.

18. The method of claim 17, wherein said determined magnetic property is selected from a group which includes coercivity, remanence, hysteresis loss, initial permeability, maximum differential permeability and differential permeability at remanence.

19. The method of claim 17 in which:
the step of determining determines a plurality of magnetic properties at each said location; and
the step of displaying assigns different colors to the false color image of the specimen by the respective derived intrinsic magnetic properties to distinguish therebetween.

* * * * *